US011453885B1

(12) United States Patent
Raji

(10) Patent No.: US 11,453,885 B1
(45) Date of Patent: Sep. 27, 2022

(54) PLANT TRANSFORMATION

(71) Applicant: Inari Agriculture Technology, Inc., Cambridge, MA (US)

(72) Inventor: Jennifer A. Raji, Waltham, MA (US)

(73) Assignee: Inari Agriculture Technology, Inc., Cambridge, MA (US)

( * ) Notice: Subject to any disclaimer, the term of this patent is extended or adjusted under 35 U.S.C. 154(b) by 0 days.

(21) Appl. No.: 16/793,140

(22) Filed: Feb. 18, 2020

Related U.S. Application Data

(60) Provisional application No. 62/807,583, filed on Feb. 19, 2019.

(51) Int. Cl.
*C12N 15/82* (2006.01)

(52) U.S. Cl.
CPC ..... *C12N 15/8205* (2013.01); *C12N 15/8213* (2013.01)

(58) Field of Classification Search
CPC .................. C12N 15/8205; C12N 15/8213
See application file for complete search history.

(56) References Cited

U.S. PATENT DOCUMENTS

| | | | |
|---|---|---|---|
| 6,384,301 | B1 | 5/2002 | Martinell et al. |
| 6,759,573 | B2 | 7/2004 | Olhoft et al. |
| 7,002,058 | B2 | 2/2006 | Martinell et al. |
| 7,473,822 | B1 | 1/2009 | Paz et al. |
| 8,030,076 | B2 | 10/2011 | Martinell et al. |
| 8,592,212 | B2 | 11/2013 | Martinell et al. |
| 2006/0260012 | A1* | 11/2006 | Khan ............... C12N 15/8205 800/312 |
| 2012/0156784 | A1* | 6/2012 | Adams, Jr. ......... C12N 15/8205 435/430 |
| 2014/0173774 | A1* | 6/2014 | Pareddy ............. C12N 15/8205 800/278 |
| 2015/0082478 | A1 | 3/2015 | Cigan et al. |
| 2019/0264218 | A1 | 8/2019 | Shultz et al. |

FOREIGN PATENT DOCUMENTS

| | | | | |
|---|---|---|---|---|
| WO | WO-2009029852 | A2 * | 3/2009 | ............. A01H 4/001 |
| WO | WO-2011095460 | A1 * | 8/2011 | ......... C12N 15/8205 |

OTHER PUBLICATIONS

Lambirth et al (A Comparison of transgenic and wild type soybean seeds: analysis of transcriptome profiles using RNA-Seq. BMC Biotechnology 15:1-17, 2015). (Year: 2015).*
Paz et al (Improved cotyledonary node method using an alternative explant derived from mature seed for efficient Agrobacterium-mediated soybean transformation. Plant Cell Rep. 25: 206-213, 2006) (Year: 2006).*
Iowa State University Plant Transformation Facility (ISUPTF, Agrobacterium-mediated transformation of soybean and recovery of transgenic soybean plants. Updated Mar. 22, 2010). (Year: 2010).*
Sato et al ( Production of Gama-Linolenic Acid and Stearidonic Acid in Seeds of Marker-Free Transgenic Soybean. Crop Sci. 44: 646-652, 2004). (Year: 2004).*
Olhoft et al (Soybean (*Glycine max*) Transformation Using Mature Cotyledonary Node Explants. Methods Mol Biol. 385-396, 2006). (Year: 2006).*
"Soybean Transformation and Regeneration Using Half-Seed Explants", Iowa State University, 2015.
"Soybean Transformation", OSU Plant Transformation Labratory Finer Laboratory at OSU, retrieved from <http://u.osu.edu/plantranslab/soybean-transformation/> on Jan. 4, 2019, 7 pages.
"Soybean Whole-Plant Transformation Half-Seed Explant", Stupar Lab, Research in Soybean Biology, retrieved from <http://stuparlab.cfans.umm.edu/protocols/soybean-whole-plant-transformation-half-seed-explant> on Jan. 4, 2019, 20 pages.
Chen et al., "High Throughput Agrobacterium tumefaciens-mediated Germline Transformation of Mechanically Isolated meristem Explants of Cotton (*Gossypium hirsutum* L.)", Plant Cell Rep., 2013, 12 pages.
Lee et al., "An Overview of Genetic Transformation of Soybean", Intech, 2012, pp. 489-506.
Olhoft et al., Soybean (*Glycine max*) Transformation Using Mature Cotyledonary Node Explants, Methods in Molecular Biology, 2006, pp. 385-396, vol. 343.
Paz et al., "Improved Cotyledonary Node Method Using an Alternative Explant Derived from mature Seed for Efficient Agrobacterium-mediated Soybean Transformation", Plant Cell Rep., 2006, pp. 206-213, vol. 25.
Paz et al., "Soybean Transformation and Regeneration Using "Half-Seed" Explants", retreived from <https://slideplayer.com/slide/8422873/> on Jan. 4, 2019.
Rech et al., "High-Efficiency Transformation by Biolistics of Soybean, Common Bean and Cotton Transgenic Plants", Nature Protocols, 2008, pp. 410-418, vol. 3, No. 3.
SAAT (Sonication assisted Agrobacterium-mediated Transformation), OSU Plant Transormation Laboratory Finer Laboratory at OSU, retrieved from <http://u.osu.edu/plantranslab/saat/> on Jan. 4, 2019, 4 pages.
Vain et al., "Osmotic Treatment Enhances Particle Bombardment-Mediated Transient and Stable Transformation of Maize", Plant Cell Reports, 1993, pp. 84-88, vol. 12.
Senapati, "A Review on Research Progress on in vitro Regeneration and Transformation of Tomato", Annual Research & Review in Biology, vol. 9(6), pp. 1-9, DOI: 10.9734/ARRB/2016/22300, 2016.

(Continued)

*Primary Examiner* — Bratislav Stankovic
*Assistant Examiner* — Wayne Zhong
(74) *Attorney, Agent, or Firm* — McKee, Voorhees & Sease, PLC

(57) ABSTRACT

Methods and systems for transforming soybean and other leguminous plants in a hypertonic media without a transition through a callus stage are provided. In certain aspects, hypertonic media used in the methods and systems do not contain a growth hormone and/or a selection agent. In certain aspects, the transformation methods and systems provide a transformation efficiency of at least about 30%.

19 Claims, No Drawings

(56) References Cited

OTHER PUBLICATIONS

Baskaran, Gene delivery using microinjection of agrobacterium to embryonic shoot apical meristem of elite indica rice cultivars, J. Plant Biochem. Biotechnol., 21(2), pp. 268-274 (doi:10.1007/s13562-011-0078-x), 2011.

Yang, "High-efficiency Agrobacterium tumefaciens mediated transformation system using cotyledonary node as explants in soybean (*Glycine max* L.)", Acta Physiologiae Plant, vol. 38, No. 60, (doi:10.1007/s11738-016-2081-2), 2016.

Buising, "Direct introduction of DNA into embryonic axes of Glycine max by microprojectile bombardment", Retrospective Theses and Dissertations, 195 Pages, 1992.

Luth, "Soybean [*Glycine max* (L.) Merr.]", Agrobacterium Protocols, vol. 1, Methods in Molecular Biology, vol. 1223, DOI: 10.1007/978-1-4939-1695-5_22, 2015.

Liu, "Efficient Agrobacterium tumefaciens-mediated transformation of soybeans using an embryonic tip regeneration system", Planta, vol. 219, pp. 1042-1049, 2004.

* cited by examiner

PLANT TRANSFORMATION

REFERENCE TO RELATED APPLICATIONS

This application claims benefit of priority to U.S. Provisional Patent Application No. 62/807,583 filed 19 Feb. 2019, which is incorporated herein by reference in its entirety

FIELD

Aspects of this disclosure relate to biotechnology, in particular compositions and methods for plant transformation.

BACKGROUND

Methods of modifying plant genomes by introducing a transgene or by targeted editing (e.g., using nucleases such as zinc-finger nucleases (ZFNs), transcription activator-like effector nucleases (TAL-effector nucleases or TALENs), and RNA-guided nucleases such as CRISPR Cas nucleases) generally have relied on transforming plant material using techniques such as *Agrobacterium*-mediated transformation or particle-mediated transformation (Biolistics). These transformation methods typically require subjecting the transformed plant material or explants to tissue culture through a dedifferentiated callus phase, and often involve selection with an antibiotic or herbicide (thus requiring the corresponding antibiotic or herbicide resistance transgene to be incorporated into the transformed plant). See, e.g., Gordon-Kamm et al. (1990) *Plant Cell*, 2:603-618. Transformed plants that contain an introduced transgene for such selection are generally subject to stringent regulatory requirements. Removal of such an introduced transgene generally requires at least one crossing or backcrossing step, which itself can introduce unwanted genomic changes in the resulting progeny plants.

Plant tissue culture as used in the production of transformed plants results in significant changes (typically a decrease) in genome methylation status and heritable epigenome changes in the resulting transformed plants; this may lead to unintended phenotypic changes or unwanted somaclonal variation in the resulting transformed plants. See, e.g., Stroud et al. (2013) eLife 2:e00354; DOI:10.7554/eLife.00354; Stelpflug et al. (2014) *Genetics*, 198:209-218. Furthermore, crop plants such as soybean are often commercially provided as "elite germplasm", or inbred lines that have been selectively bred and optimized for a given growing condition or region; not all germplasm or inbred lines are equally amenable to transformation using tissue culture.

For at least the above reasons, methods of plant transformation that do not require use of selection or tissue culture through a callus stage are advantageous.

SUMMARY

Disclosed herein are compositions and methods useful for plant transformation that do not require use of a selectable marker or of tissue culture through a callus stage.

In one aspect, the invention provides a method of providing a transformed plant, in particular a transformed leguminous plant such as a transformed soybean plant. The method includes the steps of: (a) providing a quarter-seed meristem explant that includes the whole embryo of a source seed, such as a seed of a leguminous plant or a seed of a soybean plant, wherein about one-quarter of the cotyledon is left attached to the whole embryo, wherein the shoot apical meristem tissue of the whole embryo is intact and is exposed by removal of all primary leaves, and wherein the radicle tip is trimmed; (b) contacting the quarter-seed meristem explant with a hypertonic medium; (c) contacting the explant with a suspension of a bacterial transformation vector (such as an *Agrobacterium* sp.) that contains a transformation construct; (d) co-cultivating the explant for a few days; (e) partially embedding the trimmed radicle end of the explant in shoot induction medium with the meristem side facing up and with the hypocotyl upright; (f) incubating for about 3-6 weeks with regular changes to fresh shoot induction medium; and (g) transferring to shoot elongation medium; whereby a rooted plantlet (such as a rooted leguminous plantlet or rooted soybean plantlet) that includes transformed germline cells having at least one genetic modification (in comparison to the unmodified genome of the embryo of the source seed or of the source plant from which the source seed was obtained) effected by the transformation construct is rapidly regenerated without transition through a callus phase and at a transformation efficiency of at least about 30%. The method is of use particularly in transformation of dicot plants, including leguminous plants such as soybean, cowpeas, pigeon peas, and common beans), including legumes of elite germplasm and inbred lines. The method is useful for transforming recipient plants with DNA encoding polynucleotides for sequence-specific genome editing, such as DNA encoding base editors or DNA encoding CRISPR nucleases and associated guide RNAs and donor polynucleotides. The method offers the advantages of not requiring a selection marker (e.g., an antibiotic resistance or herbicide resistance marker transgene), rapid (less than 8 weeks from inoculation) regeneration of plants directly from the explant without a callus stage, and overall high transformation efficiencies (greater than 30%). Because the method can be used in various plant species including various leguminous plant germplasms and does not require use of a selectable marker or other transgene that requires crossing or backcrossing to eliminate the marker or transgene in progeny generations, the method is particularly useful in elite germplasm or inbred lines of leguminous species (e.g., soybean). The method does not require culturing the plants through a callus phase, and therefore avoids undesirable changes associated with callus formation, such as genome hypomethylation and heritable epigenetic changes. The high transformation efficiencies observed with the method are superior to the relatively low (typically <6%) transformation efficiencies reported for other *Agrobacterium*-mediate transformation protocols used with leguminous plants; see, e.g., "*Agrobacterium* Protocols, Volume 1", Third Edition (2015), Kan Wang, editor, Springer Protocols: Methods in Molecular Biology 1223, Humana Press, Springer, New York.

Embodiments of the method further include the steps of regenerating fertile T0 plants and obtaining progeny T1 seed and T1 plants. Where the transformation involves delivery of sequence-specific genome editing molecules, the method is useful for producing T0 and progeny plants of subsequent generations that have a genome that is essentially (>99%) identical to that of the embryo of the source seed, except for the sequence-specific genome edits effected by the transformation. Also provided by the invention are transformed T0 plants and progeny plants of the T1 and further generations, including hybrid progeny plants. Because the method does not require tissue culture through a callus phase, the T0 plants (and progeny T1 seeds or T1 plants) do not exhibit the degree of epigenetic changes (such as hypomethylation) that is observed in transformed plants that are produced using tissue culture procedures that involve a callus phase.

Depending on the transformation construct(s) used, the at least one genetic modification in the transformed germline cells and the resulting T0 plants can be characterized as single or multiplexed genetic changes. For example, in embodiments of the method, the transformation construct encodes an RNA-guided nuclease such as a CRISPR Cas nuclease, and the T0 plant contains a genome that has been edited by the RNA-guided nuclease; various examples of such "genome edits" include deletion of one or more nucleotides, insertion of one or more nucleotides, insertion of a nucleotide sequence encoded by a donor polynucleotide, allele substitution or replacement, and combinations of such genomic changes. Also encompassed by the invention are raw plant materials, processed plant products, and commodity plant products obtained from a T1 plant, T1 plant cell, T1 plant tissue, or T1 seed (or from progeny plants or seeds thereof).

A related aspect provided by the invention is a system for bacterially mediated plant transformation including: (a) a dicot meristem explant that has been contacted with a hypertonic medium; and (b) a bacterial transformation vector including a transformation construct. Such a system is useful with the bacterially mediated transformation methods disclosed herein.

DETAILED DESCRIPTION OF THE INVENTION

Where a term is provided in the singular, the inventors also contemplate aspects of the invention described by the plural of that term.

"CRISPR (Clustered Regularly Interspaced Short Palindromic Repeats)/Cas (CRISPR-associated) systems," or CRISPR systems, are adaptive defense systems originally discovered in bacteria and archaea. CRISPR systems use RNA-guided nucleases termed CRISPR-associated or "Cas" endonucleases (e.g., Cas9 or Cas12a ("Cpf1")) to cleave foreign DNA. In a typical CRISPR/Cas system, a Cas endonuclease is directed to a target nucleotide sequence (e.g., a site in the genome that is to be sequence-edited) by sequence-specific, non-coding "guide RNAs" that target single- or double-stranded DNA sequences.

CRISPR-type genome editing has value in various aspects of agriculture research and development. CRISPR elements, e.g., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas12a-type endonuclease or combinations with unique PAM recognition sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cas12a (Cpf1) endonuclease and corresponding guide RNAs and PAM sites are disclosed in U.S. Pat. No. 9,790,490 and U.S. patent application Ser. No. 15/566,528 (national phase of PCT Application PCT/EP2016/058442, published as WO 2016/166340). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

At least one double-stranded break (DSB) can be effected at a precisely determined site in the plant genome, for example by means of an RNA-guided nuclease and guide RNAs, and a nucleotide sequence encoded by a donor polynucleotide can then be heterologously integrated at the site of the DSB (or between two DSBs). In embodiments, the donor polynucleotide includes single-stranded DNA, optionally including chemical modifications. In other embodiments, the donor polynucleotide includes double-stranded DNA, optionally including chemical modifications. In some embodiment the donor polynucleotide includes both DNA and RNA, for example as a duplex formed by a DNA strand and an RNA strand. In embodiments, the donor polynucleotide is designed to include a template for genome editing via homology-dependent repair (HDR); the template generally includes a "core sequence" that is to replace a sequence of the genome of about the same size, as well as "homology arms" that flank the core sequence on either side and have a sequence complementary to the genomic regions flanking the genomic sequence to be replaced or edited. In other embodiments, the donor polynucleotide does not include homology arms or does not include a core sequence and homology arms, for example in embodiments where the donor polynucleotide is used to make a deletion.

In general, a donor polynucleotide including a template encoding a nucleotide change over a region of less than about 50 nucleotides is conveniently provided in the form of single-stranded DNA; larger donor templates (e.g., more than 100 nucleotides) are often conveniently provided as double-stranded DNAs. Thus in some embodiments, the donor polynucleotide is about 25 nucleotides, 50 nucleotides, 60 nucleotides, 70 nucleotides 80 nucleotides, 90 nucleotides, 100 nucleotides, 200 nucleotides, 300 nucleotides, 400 nucleotides, 500 nucleotides, 600 nucleotides, 700 nucleotides, 800 nucleotides, 900 nucleotides, 1000 nucleotides, 1200 nucleotides, 1500 nucleotides, 1800 nucleotides, 2000 nucleotides, 2500 nucleotides, 3000 nucleotides, 5000 nucleotides, 10,000 nucleotides, or more (such as about 25-200 nucleotides, 50-300 nucleotides, 100-500 nucleotides, 200-800 nucleotides, 700-2000 nucleotides, 1000-2500 nucleotides, 2000-5000 nucleotides, 4000-8000 nucleotides, or 6000-10,000 nucleotides).

The term "heterologous" describes a nucleic acid sequence that is positioned out of its naturally occurring or native context; the term also describes two adjacent nucleic acid sequences that do not naturally occur together (but are not necessarily from different species). The term "heterologous" is also used to refer to a given sequence in relationship to another—e.g., the sequence of a donor polynucleotide molecule is heterologous to the sequence of the genomic locus wherein the polynucleotide is integrated. For example, a ubiquitin promoter sequence can be used to drive expression of a gene (for example, luciferase) other than the ubiquitin gene natively driven by the promoter; in this case the ubiquitin promoter is "heterologous" to the luciferase gene (and vice versa), and the ubiquitin promoter and luciferase gene are in a heterologous arrangement relative to each other. By "integration of heterologous sequence" is also meant integration or insertion of one or more nucleotides, resulting in a sequence (including the inserted nucleotide(s) as well as at least some adjacent nucleotides of the genomic sequence flanking the site of insertion at the DSB) that is itself heterologous, i.e., would not otherwise or does not normally occur at the site of insertion.

Whether an explant, plantlet, or T0 plant has been transformed can be determined by observing phenotype or by genotyping or by both. For the purposes of this disclosure and when referring to the claimed methods, systems, compositions, and transformed plants and seeds, "transformation efficiency" is conveniently expressed as a percentage, and is measured by dividing the total number of genotyped "positive" (that is, stably transformed) T0 plants by the total number of explants that were subjected to the transformation method, the result expressed as a percentage. Genotyping is carried out by any convenient technique, such as by PCR amplification to determine the presence of a nucleic acid sequence expected to be present in a successfully transformed plant.

Method of Providing a Transformed Plant

An aspect of this invention provides a method of providing a transformed plant, more specifically a transformed leguminous plant such as a transformed soybean plant. The method includes the steps of: (a) providing a quarter-seed meristem ("QSM") explant including the whole embryo of a source seed, such as a leguminous seed (e.g., a soybean seed), wherein one-quarter of the cotyledon is left attached to the whole embryo, and wherein the shoot apical meristem tissue of the whole embryo is intact and is exposed by removal of the primary leaves, and wherein the radicle tip is trimmed; (b) contacting the QSM explant with a hypertonic medium; (c) contacting the QSM explant with a suspension of a bacterial transformation vector such as *Agrobacterium* that includes a transformation construct; (d) co-cultivating the QSM explant; (e) partially embedding the trimmed radicle end of the QSM explant in shoot induction medium with the meristem side facing up; (f) incubating the QSM explant 3-6 weeks; and (g) transferring the QSM explant to shoot elongation medium; whereby a rooted plantlet, such as a rooted leguminous plantlet (e.g., a rooted soybean plantlet) that includes transformed germline cells having at least one genetic modification (in comparison to the unmodified genome of the embryo of the source seed or of the source plant from which the source seed was obtained) effected by the transformation construct is regenerated or grown from the QSM explant without transition through a callus phase and at a transformation efficiency of at least about 30%.

In embodiments, all of the primary leaves are removed from the QSM explant, e.g., by microdissection. In embodiments, the QSM explant is optionally wounded, e.g., by creating incisions, punctures, or abrasions (e.g., by contacting the explant with a dry abrasive or a suspension of abrasive particulates, microparticulates, or nanoparticulates) on the explant's surface. In embodiments, the radicle tip is trimmed, e.g., with a scalpel. In an embodiment, the QSM explant is obtained from a soybean (*Glycine max*) seed and the radicle tip is trimmed by 1-5 mm (typically 2-3 mm of the radicle tip is removed).

A step of the method includes contacting or pre-treating the QSM explant with a hypertonic medium ("osmotic medium"). Generally, the hypertonic medium has a higher specific osmotic pressure relative to the intercellular osmotic pressure of the meristematic tissue; osmotica useful in providing the desired osmolarity include sugars such as mannitol and sorbitol. In many embodiments the hypertonic medium includes MES (2-(N-morpholino)ethanesulfonic acid), mannitol, and sorbitol. In embodiments, the hypertonic medium includes MES, mannitol, sorbitol, and L-proline. The hypertonic medium does not require any of a number of components that are commonly used in plant tissue culture media. Specifically, the hypertonic medium does not require a growth hormone, an antioxidant, silver nitrate, or a selection agent (e.g., an antibiotic or an herbicide corresponding to a selectable resistance or marker gene used in the transformation process). Embodiments of hypertonic media include a liquid or gel or solid; in many instances it is convenient to provide the hypertonic medium as a gel or solid onto which explants may be stably positioned. Non-limiting examples of suitable hypertonic media formulations are provided in the working Examples; these illustrate suitable amounts of MES, mannitol, sorbitol, and L-proline. The QSM explant is contacted or pre-treated with the hypertonic medium for at least 30 minutes, typically between about 30 minutes to about 4 hours or for about 30 minutes to about 4 hours. In non-limiting embodiments, a soybean QSM explant is contacted with the hypertonic medium for about 30 minutes, between about 1-2 hours, about 1-2 hours, about 1-4 hours, or between about 1-4 hours.

After treatment with the hypertonic medium, the QSM explant is contacted with a bacterial transformation vector that is compatible with the plant species to be transformed. Embodiments of bacterial transformation vectors include *Agrobacterium* species, e.g., *Agrobacterium tumefaciens* and *Agrobacterium rhizogenes*. In embodiments, other bacterial transformation vectors include *Rhizobium* spp., *Mesorhizobium loti, Sinorhizobium meliloti*, and *Ensifer adhaerens*. In specific embodiments, the QSM explant is from a leguminous plant and is contacted with an *Agrobacterium* species transformation vector. In specific embodiments, the QSM explant is from a soybean plant and is contacted with an *Agrobacterium tumefaciens* transformation vector. For *Agrobacterium tumefaciens*-mediated transformation of a soybean QSM explant, the *Agrobacterium tumefaciens* culture is preferably in exponential phase growth. In embodiments, during contact of the QSM explant and the bacterial transformation vector, sonication is optionally used to enhance transformation.

The bacterial transformation vector contains or includes a transformation construct, typically a recombinant DNA construct including T-DNA borders flanking one or more DNA sequences to be integrated into the genome of the plant being transformed. In embodiments, the transformation construct includes: (a) DNA including left border and right border T-DNA sequences; (b) DNA encoding an RNA-guided nuclease; (c) DNA encoding a guide RNA; (d) DNA encoding a donor polynucleotide; or (e) a combination of any two or more of (a)-(d). In embodiments, the transformation construct includes DNA including left border and right border T-DNA sequences that flank an expression cassette (e.g., DNA including a promoter that is functional in a plant cell and is operably linked to DNA encoding a coding or a non-coding sequence to be expressed, and optionally a terminator). In embodiments, the transformation construct includes DNA including left border and right border T-DNA sequences that flank DNA encoding polynucleotides for sequence-specific genome editing, such as DNA encoding base editors or DNA encoding CRISPR nucleases and associated guide RNAs and donor polynucleotides. A specific embodiment includes an *Agrobacterium* transformation vector containing a TI (Ti) plasmid that includes left and right T-DNA border sequences flanking an expression cassette, wherein the expression cassette includes a promoter functional in a plant cell and operably linked to DNA encoding polynucleotides for sequence-specific genome editing, such as DNA encoding base editors or DNA encoding CRISPR nucleases and associated guide RNAs and donor polynucleotides. A specific embodiment includes a soybean QSM explant transformed with an *Agrobacterium* transformation vector containing a TI (Ti) plasmid that includes left and right T-DNA border sequences flanking at least one expression cassette, wherein the expression cassette includes a promoter functional in a plant cell and operably linked to DNA encoding a CRISPR nuclease, guide RNAs, and at least one donor polynucleotide; the CRISPR nuclease and guide RNAs effect one or more DSBs in the soybean genome at which the donor polynucleotide sequence is heterologously integrated.

The transformation construct does not require DNA encoding a selectable marker, such as a transgene that provides antibiotic resistance or herbicide resistance to a plant. It is possible to adapt the method to include a selection step if desirable; in such cases the transformation construct can include DNA encoding a selectable marker; however, growth of shoots and explants is typically so rapid with this method that transformed plants may be obtained before selection pressure is effective.

The quarter-seed meristem explant is co-cultivated for a period of a few days, usually less than one week. In one embodiment, a soybean quarter-seed meristem explant is co-cultivated for 4-5 days, either in the dark or under a 16 hour light/8 hour dark photoperiod cycle. Co-cultivation conditions for soybean explants typically includes a temperature of about 22 to about 26 degrees Celsius or between about 22 to about 26 degrees Celsius and about 60% to 70% humidity.

After co-cultivation, the quarter-seed meristem explant is placed on shoot induction medium for rapid, direct shoot formation without a callus phase. In the method, it is important to position the explant correctly; the trimmed radicle end of the quarter-seed meristem explant is partially embedded in shoot induction medium with the meristem side facing up and with the hypocotyl positioned approximately upright (not at an angle to the surface of the medium). (The method therefore differs from other *Agrobacterium* transformation protocols wherein the hypocotyl is positioned either at an angle to the surface of the medium, or positioned upside down with the meristem side in contact with the medium.) In one embodiment, the trimmed radicle end of a leguminous quarter-seed meristem explant is partially embedded an angle of about 45 degrees in shoot induction medium, with the meristem side facing up and the hypocotyl approximately upright. In one embodiment, the trimmed radicle end of a soybean quarter-seed meristem explant is partially embedded at an angle of about 45 degrees in shoot induction medium, with the meristem side facing up and with the hypocotyl approximately upright.

The embedded quarter-seed meristem explant is then incubated on the shoot induction medium, with regular changes to fresh shoot induction medium, to produce a shoot. In embodiments, the quarter-seed meristem explant is incubated for less than 8 weeks on shoot induction medium to produce a shoot. In embodiments, the shoot induction medium is changed periodically. In an embodiment, a leguminous shoot develops from the leguminous quarter-seed meristem explant that has been incubated 3-6 weeks on shoot induction medium, with approximately biweekly changes to fresh shoot induction medium. In an embodiment, a soybean shoot develops from the soybean quarter-seed meristem explant that has been incubated 3-6 weeks on shoot induction medium, with biweekly changes to fresh shoot induction medium. In an embodiment, a soybean shoot develops from the soybean quarter-seed meristem explant that has been incubated for about 3, or slightly less than 3 weeks, on shoot induction medium, with 1 or 2 changes to fresh shoot induction medium during the incubation period.

Following incubation on shoot induction medium, the shoot is transferred to shoot elongation medium to produce a rooted plantlet, such a rooted leguminous plantlet or a rooted soybean plantlet. A separate rooting medium is not required. The shoot, and the rooted plantlet developed from the shoot, includes transformed germline cells having at least one genetic modification, in comparison to the unmodified genome of the embryo of the source seed, wherein the at least one genetic modification was effected by the transformation construct. In embodiments, a rooted plantlet is rapidly regenerated, without transition through a callus phase and at a transformation efficiency of at least about 30%. In embodiments, the rooted plantlet is transferred into soil for further growth. In a specific embodiment, a rooted leguminous plantlet is regenerated within less than 8 weeks (e.g., within 3-6 weeks) from the time of inoculation, without transition through a callus phase and at a transformation efficiency of at least about 30%, e.g., at least 30%, at least about 40%, at least about 50%, or at least about 60%. In a specific embodiment, a rooted soybean plantlet is regenerated within less than 8 weeks (e.g., within 3-6 weeks) from the time of inoculation, without transition through a callus phase and at a transformation efficiency of at least about 30%, e.g., at least 30%, at least about 40%, at least about 50%, or at least about 60%. In a specific embodiment, a rooted soybean plantlet is regenerated within about 3 weeks from the time of inoculation, without transition through a callus phase and at a transformation efficiency of at least about 50%.

The transformation method is of use in dicots, particularly leguminous plants (family Fabaceae or Leguminosae) such as legumes grown for human or animal consumption (e.g., peas, beans, lentils, soybean, and forage legumes). Non-limiting examples of plants suited for the transformation method include soybean (*Glycine max*), *Vigna* spp., such as cowpea or black-eyed pea (*Vigna unguiculate*), adzuki bean (*Vigna angularis*), black gram (*Vigna mungo*), mung bean (*Vigna radiata*), and groundnut (*Vigna subterranea*), *Cajanus* spp., such as pigeon pea (*Cajanus cajan*), and common bean (*Phaseolus* spp.) varieties. Embodiments of the transformation method include those wherein the resulting transformed rooted plantlet or transformed plant is a transformed soybean plantlet or plant. In embodiments, the transformed soybean plantlet or plant is of an elite soybean germplasm, or is of an inbred soybean line.

In embodiments, the source seed is an immature seed, or is a mature seed (typically imbibed), or is a germinated seed. In an embodiment, the source seed is a soybean seed selected from the group consisting of: (a) an immature soybean seed; (b) a mature, imbibed soybean seed; and (c)

a germinated soybean seed (e.g., a soybean seed that has been germinated about 1 day to about 1 week or between about 1 day to about 1 week).

Embodiments of the method provide the advantage of not requiring a selection step, such as selection using an antibiotic or an herbicide, and in such embodiments the various media used in transformation and culture do not include a selection agent such as an antibiotic or an herbicide. However, other embodiments of the method further include a selection step; in these cases, a selectable marker gene (such as an antibiotic resistance gene or an herbicide resistance gene) may be included in the transformation construct and one or more of the media used in transformation and culture may contain the appropriate selection agent.

In general, the transformation method described here results in fertile regenerated plantlets, e.g., fertile leguminous plantlets or fertile soybean plantlets. In embodiments the method provides fertile leguminous plantlets including transformed germline cells having at least one genetic modification, in comparison to the unmodified genome of the embryo of the source leguminous seed, wherein the at least one genetic modification was effected by the transformation construct. In embodiments the method provides fertile soybean plantlets including transformed germline cells having at least one genetic modification, in comparison to the unmodified genome of the embryo of the source soybean seed, wherein the at least one genetic modification was effected by the transformation construct. In these embodiments, the transformed germline cells having at least one genetic modification can give rise to further generations of transformed seeds and plants that also contain the at least one genetic modification in their genome.

Embodiments of the method further include the step of growing the regenerated plantlet (such as a transformed fertile leguminous plantlet or a transformed fertile soybean plantlet) to maturity, thus providing a mature transformed (T0) plant (such as a mature transformed T0 leguminous plant or a mature transformed T0 soybean plant). In embodiments, the mature transformed T0 leguminous plant has a genome that contains the at least one genetic modification and that is greater than 99.9% identical to that of the embryo of the source leguminous seed. In specific embodiments, the mature transformed T0 soybean plant has a genome that contains the at least one genetic modification and that is greater than 99.9% identical to that of embryo of the source soybean seed.

Embodiments of the method further include the step of recovering progeny (T1) seeds from the mature transformed (T0) plant, such as recovering progeny (T1) leguminous seeds from the mature transformed (T0) leguminous plant or recovering progeny (T1) soybean seeds from the mature transformed (T0) soybean plant. Additional embodiments of the method further include the step of growing a progeny transformed (T1) plant from the T1 seed, such as growing a progeny transformed (T1) leguminous plant from the T1 leguminous seed or growing a progeny transformed (T1) soybean plant from the T1 soybean seed. Thus, related aspects of the invention include the mature transformed T0 plants, progeny T1 seeds, and progeny T1 plants, all of which contain the at least one genetic modification, in comparison to the unmodified genome of the embryo of the source seed, wherein the at least one genetic modification was effected by the transformation construct in the explant that was regenerated into the mature transformed T0 plant. Embodiments include the mature transformed T0 leguminous plants, progeny T1 leguminous seeds, and progeny T1 leguminous plants, all of which contain the at least one genetic modification, in comparison to the unmodified genome of the embryo of the source leguminous seed, wherein the at least one genetic modification was effected by the transformation construct in the leguminous quarter-seed meristem explant that was regenerated into the mature transformed T0 leguminous plant. Specific embodiments include the mature transformed T0 soybean plants, progeny T1 soybean seeds, and progeny T1 soybean plants, all of which contain the at least one genetic modification, in comparison to the unmodified genome of the embryo of the source soybean seed, wherein the at least one genetic modification was effected by the transformation construct in the soybean quarter-seed meristem explant that was regenerated into the mature transformed T0 soybean plant.

In embodiments, the method provides a regenerated transformed ("T0") plant (such as a regenerated transformed T0 leguminous plant or a regenerated transformed T0 soybean plant) containing at least one genetic modification effected by the transformation agent that is absent in the embryo of the source seed (or of the source plant from which the source seed was obtained); depending on the transformation agents used, the genetic modification can be variously characterized as transient transformation, stable genomic changes, gene editing (genome editing), base editing; single or multiplexed genetic changes. In embodiments of the method, the transformation agent includes an RNA-guided nuclease, and the T0 plant contains a genome that has been edited by the RNA-guided nuclease; specific embodiments include a T0 leguminous plant or a T0 soybean plant that contains in its genome one or more "genome edits" such as deletion of one or more nucleotides, insertion of one or more nucleotides, insertion of a nucleotide sequence encoded by a donor polynucleotide, allele substitution or replacement, and combinations of such genomic changes.

In embodiments, the regenerated transformed T0 plant provided by the method has a genome that is greater than 99.9% identical to that of the embryo of the source seed. Because the method does not require tissue culture through a callus phase, the T0 plant (and progeny T1 seeds or T1 plants) do not exhibit the degree of epigenetic changes (such as hypomethylation) that is observed in transformed plants that are produced using tissue culture through a callus phase. Thus, the genome of a regenerated stably transformed T0 plant (and progeny T1 seeds or T1 plants) provided by the method differs significantly from the genome of a plant obtained by traditional breeding (i.e., crossing of a male parent plant and a female parent plant), where unwanted and random exchange of genomic regions as well as random mitotically or meiotically generated genetic and epigenetic changes in the genome typically occurs during the parental cross and are then found in the progeny plants. In embodiments, the genome of a stably transformed T0 plant provided by the method or of the progeny T1 seeds or plants is more than 99.9% identical to the genome of the embryo of the source seed. In embodiments, the genome of a stably transformed T0 leguminous plant or T1 leguminous seeds or plants provided by the method is devoid of random mitotically or meiotically generated genetic or epigenetic changes relative to the genome of the embryo of the source leguminous seed. In specific embodiments, the genome of a stably transformed T0 soybean plant or T1 soybean seeds or plants provided by the method is devoid of random mitotically or meiotically generated genetic or epigenetic changes relative to the genome of the embryo of the source soybean seed. In embodiments, the genome of a stably transformed T0 plant or T1 seeds or plants provided by the method includes a difference of epigenetic changes in less than 0.01% of the genome relative to the genome of the embryo of the source seed. In embodiments, the genome of a stably transformed leguminous T0 plant or T1 seeds or plants provided by the method includes a difference of epigenetic changes in less than 0.01% of the genome relative to the genome of the embryo of the source leguminous seed. In specific embodiments, the genome of a stably transformed soybean T0 plant or T1 seeds or plants provided by the method includes a difference of epigenetic changes in less than 0.01% of the genome relative to the genome of the embryo of the source soybean seed. In embodiments, the genome of a stably transformed T0 plant or T1 seeds or plants provided by the method includes: (a) a difference of DNA methylation in less than 0.01% of the genome, relative to the genome of the embryo of the source plant; or (b) a difference of DNA methylation in less than 0.005% of the genome, relative to the genome of the embryo of the source plant; or (c) a difference of DNA methylation in less than 0.001% of the genome, relative to the genome of the embryo of the source plant. In embodiments of the method, a gene of interest located on a given chromosome in cells of the source plant is specifically targeted for editing or mutation (e.g. using a sequence-specific nuclease such as a CRISPR nuclease), and the genome of the resulting stably transformed T0 plant or T1 seeds or plants includes: (a) a difference of DNA methylation in less than 0.01% of the portion of the genome that is contained within the chromosome containing the gene of interest, relative to the genome of the embryo of the source plant; or (b) a difference of DNA methylation in less than 0.005% of the portion of the genome that is contained within the chromosome containing the gene of interest, relative to the genome of the embryo of the source monocot plant; or (c) a difference of DNA methylation in less than 0.001% of the portion of the genome that is contained within the chromosome containing the gene of interest, relative to the genome of the embryo of the source monocot plant. In embodiments, the genome of a stably transformed T0 plant or T1 seeds or plants provided by the method has not more unintended changes in comparison to the genome of the embryo of the source seed (or of the source plant from which the source seed was obtained) than $1 \times 10^{-8}$ mutations per base pair per replication.

System for Bacterially Mediated Plant Transformation

An aspect of this invention provides a system for bacterially mediated plant transformation including: (a) a dicot (such as a legume or soybean) meristem explant that has been contacted with or pre-treated with a hypertonic medium, and (b) a bacterial transformation vector including a transformation construct.

In embodiments, the dicot meristem explant is obtained from a leguminous plant, such as a soybean plant. In embodiments, the dicot meristem explant is a shoot apical meristem explant obtained from the embryo of a dicot seed or from a germinated dicot seedling. In embodiments, the dicot meristem explant is a meristem explant including the embryo of a source dicot seed, with part of the cotyledon removed. In a specific embodiment, the dicot meristem explant is a quarter-seed meristem explant including the whole embryo of a source seed, such as a leguminous seed (e.g., a soybean seed), wherein one-quarter of the cotyledon is left attached to the whole embryo, and wherein the shoot apical meristem tissue of the whole embryo is intact and is exposed by removal of the primary leaves, and wherein the radicle tip is trimmed.

The dicot meristem explant has been contacted with or pre-treated with a hypertonic medium ("osmotic medium"). In embodiments, the dicot meristem explant has been contacted with or pre-treated with the hypertonic medium for at least 30 minutes, for example, for about 30 minutes, about 1 hour, about 1.5 hours, about 2 hours, about 1 to 4 hours, or between 1 to 4 hours. Generally, the hypertonic medium has a higher specific osmotic pressure relative to the intercellular osmotic pressure of the meristematic tissue; osmotica useful in providing the desired osmolarity include sugars such as mannitol and sorbitol. In many embodiments the hypertonic medium includes MES (2-(N-morpholino) ethanesulfonic acid), mannitol, and sorbitol. In embodiments, the hypertonic medium includes MES, mannitol, sorbitol, and L-proline. The hypertonic medium does not require any of a number of components that are commonly used in plant tissue culture media. Specifically, the hypertonic medium does not require a growth hormone, an antioxidant, silver nitrate, or a selection agent (e.g., an antibiotic or an herbicide corresponding to a selectable resistance or marker gene used in the transformation process). Embodiments of hypertonic media include a liquid or gel or solid; in many instances it is convenient to provide the hypertonic medium as a gel or solid onto which explants may be stably positioned. Non-limiting examples of suitable hypertonic media formulations are provided in the working Examples; these illustrate suitable amounts of MES, mannitol, sorbitol, and L-proline. In embodiments where the transformation system is employed with a transformation protocol that includes selection (e.g., by transformation with a transgene conferring resistance to an antibiotic or an herbicide), the appropriate selection agent can be included in the hypertonic medium.

An embodiment of the transformation system includes (a) a dicot meristem explant that has been contacted or pre-treated for at least 30 minutes with a hypertonic medium that includes MES and at least one osmoticum selected from the group consisting of mannitol and sorbitol, and that does not include a growth hormone, silver nitrate, or an antioxidant, and (b) a bacterial transformation vector including a transformation construct. Another embodiment of the transformation system includes (a) a leguminous (e.g., soybean) meristem explant that has been contacted or pre-treated for 30 minutes to 4 hours or between 30 minutes to 4 hours with a hypertonic medium that includes MES, L-proline, and at least one osmoticum selected from the group consisting of mannitol and sorbitol, and that does not include a growth hormone, silver nitrate, an antioxidant, or a selection agent, and (b) a bacterial transformation vector including a transformation construct. One specific embodiment of the transformation system includes (a) a leguminous (e.g., soybean) quarter-seed meristem explant that has been contacted for at least 30 minutes with a hypertonic medium that includes MES, at least one osmoticum selected from the group consisting of mannitol and sorbitol, and optionally L-proline, and that does not include a growth hormone or a selection agent, and (b) an *Agrobacterium* transformation vector including a transformation construct.

The system for bacterially mediated plant transformation further includes a bacterial transformation vector that includes or contains a transformation construct. The bacterial transformation vector is selected for compatibility with the plant species to be transformed. Embodiments of bacterial transformation vectors include *Agrobacterium* species, e.g., *Agrobacterium tumefaciens* and *Agrobacterium rhizogenes*. In embodiments, other bacterial transformation vectors include *Rhizobium* spp., *Mesorhizobium loti*, *Sinorhizobium meliloti*, and *Ensifer adhaerens*. The bacterial transformation vector contains or includes a transformation construct, typically a recombinant DNA construct including T-DNA borders flanking one or more DNA sequences to be integrated into the genome of the plant being transformed. In embodiments, the transformation construct includes: (a) DNA including left border and right border T-DNA sequences; (b) DNA encoding an RNA-guided nuclease; (c) DNA encoding a guide RNA; (d) DNA encoding a donor polynucleotide; or (e) a combination of any two or more of (a)-(d). In embodiments, the transformation construct is provided as part of an *Agrobacterium* TI (Ti) plasmid. In embodiments, the transformation construct includes DNA including left border and right border T-DNA sequences that flank an expression cassette (e.g., DNA including a promoter that is functional in a plant cell and is operably linked to DNA encoding a coding or a non-coding sequence to be expressed, and optionally a terminator). In embodiments, the transformation construct includes DNA including left border and right border T-DNA sequences that flank DNA encoding polynucleotides for sequence-specific genome editing, such as DNA encoding base editors or DNA encoding CRISPR nucleases and associated guide RNAs and donor polynucleotides. A specific embodiment includes an *Agrobacterium* transformation vector containing a TI (Ti) plasmid that includes left and right T-DNA border sequences flanking an expression cassette, wherein the expression cassette includes a promoter functional in a plant cell and operably linked to DNA encoding polynucleotides for sequence-specific genome editing, such as DNA encoding base editors or DNA encoding CRISPR nucleases and associated guide RNAs and donor polynucleotides. One specific embodiment of the transformation system includes (a) a leguminous (e.g., soybean) quarter-seed meristem explant that has been contacted for at least 30 minutes with a hypertonic medium that includes MES and L-proline and does not include a growth hormone, and (b) an *Agrobacterium tumefaciens* transformation vector containing a TI (Ti) plasmid that includes left and right T-DNA border sequences flanking an expression cassette, wherein the expression cassette includes a promoter functional in a plant cell and operably linked to DNA encoding polynucleotides for sequence-specific genome editing.

Related Disclosure

Plants of Interest: The methods, compositions, and systems disclosed herein are useful in bacterially mediated transformation of dicot plants, in particular leguminous plants (family Fabaceae or Leguminosae) such as legumes grown for human or animal consumption (e.g., peas, beans, lentils, soybean, and forage legumes), including, but not limited to, *Phaseolus* spp., *Vigna* spp., *Vicia* spp., *Pisum* spp., *Lens* spp., *Medicago* spp., and *Trifolium* spp. Non-limiting examples of plants suited to the transformation methods and systems disclosed herein include soybean (*Glycine max*), *Vigna* spp., such as cowpea or black-eyed pea (*Vigna unguiculate*), adzuki bean (*Vigna angularis*), black gram (*Vigna mungo*), mung bean (*Vigna radiata*), and groundnut (*Vigna subterranea*), *Cajanus* spp., such as pigeon pea (*Cajanus cajan*), chickpea (*Cicer arietinum*), and common bean (*Phaseolus* spp.) varieties.

Transformation Constructs and Vectors: Plasmids designed for use in plants and encoding CRISPR genome editing elements (CRISPR nucleases and guide RNAs) are publicly available from plasmid repositories such as Addgene (Cambridge, Mass.; also see "addgene[dot]com") or can be designed using publicly disclosed sequences, e. g., sequences of CRISPR nucleases. In embodiments, such plasmids are used to co-express both a CRISPR nuclease mRNA and guide RNA(s); in other embodiments, a CRISPR nuclease mRNA and guide RNA are encoded on separate plasmids. In embodiments, the plasmids are *Agrobacterium* TI (Ti) plasmids useful as the transformation construct of the methods and systems disclosed herein. Materials and methods for preparing expression cassettes and vectors for CRISPR endonuclease and guide RNA for stably integrated and/or transient plant transformation are disclosed in PCT/US2015/018104 (published as WO/2015/131101 and claiming priority to U.S. Provisional Patent Application 61/945, 700), US Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In embodiments, the expression cassette is adjacent to or located between T-DNA borders or contained within a binary vector, e. g., for *Agrobacterium*-mediated transformation. In embodiments, the transformation construct of the methods and systems disclosed herein includes (a) DNA encoding a CRISPR nuclease and (b) DNA encoding one or multiple guide RNAs; the transformation construct optionally includes DNA encoding one or more donor polynucleotides.

EXAMPLES

Example 1

This example illustrates several embodiments of media useful in the transformation methods and systems described herein, wherein a dicot meristem explant (such as a quarter-seed meristem explant of a legume, e.g., soybean) is contacted with or pre-treated with a hypertonic medium. More specifically, this example provides recipes for a hypertonic medium ("osmotic medium") that includes MES (2-(N-morpholino)ethanesulfonic acid) and at least one osmoticum selected from the group consisting of mannitol and sorbitol, and optionally includes L-proline, and that generally does not include a growth hormone, an antioxidant, silver nitrate, or a selection agent.

Table 1 provides non-limiting examples of hypertonic media formulations that are suited for use in the transformation methods and systems described herein, and illustrate suitable ranges of various components. The components and amounts required to make the base medium are listed (quantities given are for 1 liter of medium). Final pH values are also provided. The formulations as provided here are for a solid medium with Nobel agar as the gelling agent. Other suitable gelling or solidifying agents include Gelrite (catalogue number G35020, Research Products International, Mt. Prospect, Ill.) and Phytagel (P8169, Sigma, St. Louis, Mo.). The hypertonic medium can alternatively be prepared as a liquid. To prepare 1 litre of medium, the appropriate amount of each component is added to 800 mL of distilled or deionized water and the mixture placed on a magnetic stirrer until all components are fully dissolved. The pH is adjusted to 5.7 and distilled water added to make volume up to 1 L. The mixture is autoclaved at 121 degrees Celsius for 25 minutes. The autoclaved medium is cooled to 60-65 degrees Celsius and then poured into petri plates (100 mm×25 mm) under sterile conditions. The plates are allowed to dry and then stored at room temperature for up to 2 weeks, or at 4 degrees Celsius for up to 6 weeks.

TABLE 1

Hypertonic Media Formulations*

| Component (in grams) | Formula | | | | | | | | | |
|---|---|---|---|---|---|---|---|---|---|---|
| | 1 | 2 | 3 | 4 | 5 | 6 | 7 | 8 | 9 | 10 |
| B5 Medium (G398, Phytotech Laboratories, Lenexa, KS) | 4.3 | 4.3 | 4.3 | 4.3 | 4.3 | 4.3 | 4.3 | 4.3 | 4.3 | 4.3 |
| Sucrose (S8501, Sigma, St. Louis, MO) | 30 | 30 | 35 | 30 | 35 | 30 | 20 | 30 | 20 | 30 |
| MES (M3671, Sigma, St. Louis, MO) | 0.40 | 0.59 | 0.70 | 0.59 | 0.50 | 0.59 | 0.50 | 0.59 | 0.69 | 0.69 |
| Noble agar (A5431, Sigma, St. Louis, MO) | 7 | 7 | 7 | 7 | 7 | 7 | 7 | 6 | 6 | 6 |
| Mannitol (M4125, Sigma, St. Louis, MO) | 34.5 | 37.0 | 40.5 | 37.0 | 35.0 | 40.0 | 37.0 | 40.0 | 30.0 | 30.0 |
| Sorbitol (S1876, Sigma, St. Louis, MO) | 34.5 | 37.0 | 40.5 | 37.0 | 40.0 | 35.0 | 37.0 | 40.0 | 30.0 | 30.0 |
| L-Proline (P5607, Sigma, St. Louis, MO) | 0.25 | 0.50 | 0.90 | 0 | 0.50 | 0 | 0.75 | 0.50 | 0.30 | 0 |

*For any of these formulations, optionally, after autoclaving, the medium is cooled to 65 degrees Celsius and one or more of the following is added per L: 1.0-1.2 mg 6-benzylaminopurine ("BAP", 1214-39-7, Phytotech Laboratories, Lenexa, KS), 100 mg Timentin (T869, Phytotech Laboratories, Lenexa, KS), 50 mg Cefotaxime (C380, Phytotech Laboratories, Lenexa, KS).

Table 2 provides examples of various media formulations suitable for use in the transformation methods and systems described herein. The components and amounts required to make the base medium are listed (quantities given are for 1 liter of medium). To prepare 1 litre of medium, the appropriate amount of each component is added to 800 mL of distilled or deionized water and the mixture placed on a magnetic stirrer until all components are fully dissolved. The pH is adjusted as indicated and distilled water is added to make volume up to 1 L. The mixture is autoclaved at 121 degrees Celsius for 25 minutes and then cooled. Antibiotics and other heat-sensitive components are added at this point as indicated in Table 2. For solid media, the autoclaved medium is cooled to 60-65 degrees Celsius and poured into Petri plates (100 mm×20 mm; 20 plates per liter of medium) under sterile conditions. Plates are allowed to dry and then are stored at room temperature for up to 2 weeks, or at 4 degrees Celsius for up to 6 weeks. While the transformation methods, systems, and compositions do not require use of a selectable marker (e.g., a transgene providing antibiotic or herbicide tolerance), including selection during culture is optional; if the explants have been transformed with a transformation construct including a selectable marker, the medium should contain the appropriate selection agent.

TABLE 2

Tissue Culture Media

| Component | Co-cultivation medium | Shoot induction medium | Shoot elongation medium | Rooting medium |
|---|---|---|---|---|
| B5 Medium (g) | 4.3 | 4.3 | 4.3 | 4.3 |
| Sucrose (g) | 30 | 30 | 30 | 20 |
| MES (g) | 0.59 | 0.59 | 0.59 | 0.59 |
| Noble agar (g) | — | 7 | 7 | 7 |
| Asparagine (mg) (5794-13-8, Phytotech Laboratories, Lenexa, KS) | — | — | 50 | — |
| pH | 5.7 | 5.7 Add after cooling: | 5.7 Add after cooling: | 5.6 Add after cooling: |
| BAP (mg) | — | 1.11 | 0.5 | — |
| Kanamycin (mg) | — | 100* | 100 | — |
| Timentin (mg) | — | 100* | 100 | — |
| Cefotaxime (mg) | — | 50 | 50 | — |
| L-Pyroglutamic acid (mg) (04-2401, Indofine Chemical Co., Hillsborough, NJ) | — | — | 100 | — |
| Indole-3-acetic acid (IAA) (mg) (87-51-4, Phytotech Laboratories, Lenexa, KS) | — | — | 0.1 | — |
| Gibberellic acid (GA3) (mg) (77-06-5, Phytotech Laboratories, Lenexa, KS) | — | — | 0.5 | — |
| Indole-3-butyric acid (IBA) (I538, Phytotech Laboratories, Lenexa, KS) (mg) | — | — | — | 1.0 |

*Optional

Example 2

This example illustrates a non-limiting embodiment of a plant transformation method that includes the steps of: (a) providing a quarter-seed meristem ("QSM") explant that includes the whole embryo of a source seed, such as a seed of a leguminous plant or a seed of a soybean plant, wherein about one-quarter of the cotyledon is left attached to the whole embryo, wherein the shoot apical meristem tissue of the whole embryo is intact and is exposed by removal of all primary leaves, and wherein the radicle tip is trimmed; (b) contacting the QSM explant with a hypertonic medium; (c) contacting the QSM explant with a suspension of a bacterial transformation vector that contains a transformation construct; (d) co-cultivating the QSM explant for a few days; (e) partially embedding the trimmed radicle end of the QSM explant in shoot induction medium with the meristem side facing up and with the hypocotyl upright; (f) incubating the QSM explant 3-6 weeks with regular changes to fresh shoot induction medium; and (g) transferring the QSM explant to shoot elongation medium; whereby a rooted plantlet (such as a rooted leguminous plantlet or rooted soybean plantlet) that includes transformed germline cells having at least one genetic modification (in comparison to the unmodified genome of the embryo of the source seed or of the source plant from which the source seed was obtained) effected by the transformation construct is rapidly regenerated from the QSM explant without transition through a callus phase and at a transformation efficiency of at least about 30%. More specifically, this example illustrates use of the transformation method with *Agrobacterium tumefaciens* as the bacterial vector to provide stably transformed *Glycine max* rooted plantlets within 8 weeks or less from the date of *Agrobacterium* inoculation and at a transformation efficiency of at least 30%.

In the transformation protocol, mature soybean seed are conveniently used. However, immature soybean seed can be used. A general protocol for mature seed preparation is described here: Place about 100 mature soybean seeds in 15×100 mm petri plates and arrange them in stacks of 3-6 in a desiccator placed inside a fume hood. Pour about 100 mL of bleach into a beaker in the desiccator and add 4-5 ml of 12N HCL using a pipette. Close the desiccator and leave for at least 16-18 hours to sterilize the seeds. After sterilization, cover petri plates and seal with parafilm. Sterilized seeds can be stored at room temperature for up to 2 months.

A general protocol for quarter-seed meristem ("QSM") explant preparation from sterilized mature soybean seeds is described here. The aim is to prepare an explant that includes the whole embryo with an exposed but intact meristem attached to half of a single cotyledon. Sterilized mature soybean seeds are completely immersed in autoclaved sterile water in a sterile petri plate at room temperature, and allow to imbibe in a laminar flow hood overnight. The next day, the sterilized seeds are rinsed 2-3 times with autoclaved sterile water prior to dissection. The seed is held in place with a pair of curved tip forceps, the seed coat is removed, and the two cotyledons carefully separated from each other with one cotyledon removed completely and discarded. Leaving the whole embryo attached to the upper part of the remaining cotyledon, the lower half of that cotyledon is cut off with a scalpel. Under a stereomicroscope, about 3 mm of the radicle tip is cut off and all primary leaves around the meristem are removed; this results in a QSM explant ready for the transformation methods described herein. (An optional step is to allow the leaf primordia about 24 hours of growth in a dark incubator to make it easier to see and remove the leaf primordial tissue.) This QSM explant preparation protocol is adapted as necessary for immature seeds or germinated seeds, or for explants from seeds of other leguminous plants; in all cases the leaf primordia or buds are removed from the QSM explant and the radicle is trimmed.

Transfer the prepared QSM explants to liquid or solid hypertonic medium (see Example 1) and incubate for at least 30 minutes (e.g., 1 hour, 2 hours, 3 hours, or 4 hours) prior to inoculation with *Agrobacterium*.

For inoculation, use 50 mL of an *Agrobacterium* culture grown in YEB medium to an optical density of 0.8-1.0, pelleted, and gently resuspended in a 50 mL tube by pipetting in 25 mL inoculation medium; add 25 microliters 100 mM acetosyringone just prior to inoculating the explants. Transfer the QSM explants that have been pretreated with hypotonic medium to the tube containing the *Agrobacterium* suspension and mix. Sonication (1-2 minutes in an ultrasonic bath) of the tube is optional. Transfer the QSM explant/*Agrobacterium* mixture to a sterile Petri plate and seal with Parafilm; incubate at room temperature on a shaker (100 rpm) for about 30 minutes. Remove the *Agrobacterium* suspension from the QSM explants and transfer the explants to sterile filter paper pre-soaked with inoculation medium. Co-cultivate 4-5 days either in the dark or using a 16 hour light/8 hour dark photoperiod, 22-26 degrees Celsius, 60-70% humidity.

Following co-cultivation, transfer the QSM explants (7 per plate) to shoot induction medium (see Example 1). When positioning the QSM explants on the medium, the trimmed radicle end of the explant is partially embedded in shoot induction medium with the meristem side facing up and with the hypocotyl positioned approximately upright (i.e., not at an angle to the surface of the medium). The QSM explant should not be positioned upside down or with the meristem side in contact with the medium. For soybean, the trimmed radicle end of a soybean QSM explant is partially embedded at an angle of about 45 degrees in shoot induction medium, with the meristem side facing up and with the hypocotyl approximately upright. This positioning is done to encourage direct shoot primordia growth from the shoot apical meristem, without the formation of callus. Each plate is wrapped with micropore tape and incubated at about 24-28 degrees Celsius under a 16 hour light/8 hour dark photoperiod, for about 3 weeks to about 6 weeks (typically about 4 weeks), with approximately biweekly transfers to fresh shoot induction medium.

Because shoot formation from the QSM explants is so rapid using this transformation method, use of rooting medium is not required (although it may optionally be used if root emergence is delayed). Growing shoots are transferred at about 3-4 cm shoot length to shoot elongation medium. With soybean, the method results in rooted shoots as early as the third week and generally by the fifth week after inoculation, without use of rooting medium.

When the plantlets are between 3-6 cm (shoot height from surface of medium) in size, they are typically transferred to prepared "Jiffy" pots filled with soil for hardening and acclimation. Flats of transplanted plantlets are covered with a humidity dome and grown in a growth chamber at about 25 (+/−3) degrees Celsius and about 70% humidity under a 16 hour light/8 hour dark photoperiod, for about 10-14 days, watered as needed. The humidity dome vents are opened after about 4 days and the humidity dome removed after about 8 days. When plantlets are fully established, they can be transplanted to bigger pots as required.

This transformation process using the QSM explants and method described here is rapid and efficient, with the time spent in tissue culture (i.e., from inoculation to transfer to soil for hardening and acclimation) taking only about 3-6 weeks in total, and overall transformation efficiencies of at least 30%, and frequently at least 50% or higher. The method does not employ culturing the explants through a callus phase, thus avoiding undesirable changes in genome methylation status or other heritable epigenome changes in the resulting transformed plants.

Example 3

This example illustrates use of the transformation method, system, and compositions as described in Examples 1 and 2 to provide *Agrobacterium*-transformed soybean plants without use of selection or growth through a callus stage, with overall transformation efficiencies greater than 30%.

Transformation of QSM explants obtained from mature soybean seeds was carried out using the procedure and materials described in Examples 1 and 2. The soybean varieties tested included Williams 82 and a commercial cultivar. Initial experiments with the QSM transformation protocol showed no difference between the soybean varieties in terms of regeneration and plant recovery. The bacterial transformation vector was *Agrobacterium tumefaciens* (strain GV3101), containing a transformation construct including a T-DNA expression cassette for expressing one of two proteins (#013 and #014). Expression of protein #013 provides an observable (visible) phenotype. The QSM explants transformed with the protein #014 construct were examined for transient expression 4 days after inoculation; a positive phenotype was observed in more than 90% of the explants, for both transformed Williams 82 and the transformed commercial cultivar, indicating that the different soybean lines responded similarly to the transformation method.

Three experimental groups of QSM explants (Williams 82 variety), transformed with either the #013 or #014 constructs, were grown on into T0 plantlets. All T0 plants were fully rooted and ready for transfer to soil-filled Jiffy pots at 21 days (3 weeks after inoculation) for further growth. A small piece of leaf tissue was collected for molecular analysis from subsets of T0 plants while they were still in Jiffy pots (8 weeks post-inoculation); genomic DNA was isolated and analysed by PCR to screen for the appropriate transgenic protein. Results for each of the three experiments are provided in Table 3. In each experiment, the PCR results confirmed expression of the transgenic protein in between 56-78% of the T0 (relative to the total number of explants subjected to the transformation method) plants, indicating stable transformation of a majority of the T0 plants. The PCR-amplified fragment was purified from a few of the PCR-positive plants and sequenced to confirm the correct protein sequences.

TABLE 3

| | Experiment | | |
|---|---|---|---|
| | A | B | C |
| Protein expressed | #013 | #014 | #013 |
| Total number of QSM explants | 150 | 150 | 60 |
| Number of hardened-off T0 plants | 125 | 128 | 56 |
| Number of T0 plants genotyped | 92 | 62 | 41 |
| PCR-positive T0 plants | 72 | 41 | 23 |
| PCR-negative T0 plants | 20 | 21 | 18 |
| Percent genotyped-positive T0 plants | 78% | 66% | 56% |

A number of T0 plants transformed with the #013 construct were grown to maturity for seed production. The plants appeared morphologically normal and the seeds also appeared normal. Immature T1 seeds were harvested from the PCR-positive T0 plants for genotyping; seeds were sampled across different pods to obtain 12 seeds per plant which were analysed for the presence of the transgene encoding protein #013. In 16 out of 17 PCR-positive T0 plants, at least one seed was confirmed by PCR to contain the transgene. In 6 out of 17 PCR-positive T0 plants, the PCR results confirmed presence of the transgene in at least 43% of seeds indicating that the seeds were produced by a bona fide transgenic T0 plant. In 6 out of 17 PCR-positive T0 plants, the PCR results showed presence of the transgene at only low frequencies in T1 seed, indicating that the T0 plants were likely chimeric. Overall, the results demonstrate that T0 plants and T1 seed transgenic for protein #013 were successfully obtained by *Agrobacterium tumefaciens*-mediated transformation of soybean quarter-seed meristem explants, with rapid (~3 weeks from inoculation), direct regeneration of rooted plantlets from the explants without a callus phase and without selection, and with a transformation efficiency (calculated as the total number of genotyped "positive" T0 plants by the total number of explants that were subjected to the transformation method) of greater that 50%.

In separate experiments, transformation compositions, systems, and methods similar to those described in Examples 1-3 are used to stably transform other legumes including cowpea (*Vigna unguilculata*) and common bean (*Phaseolus* sp.) with similar results to that described here for soybean.

Various embodiments of the methods, systems, and compositions provided herein are described in the following non-limiting list of embodiments.

Embodiment 1: A method of providing a transformed leguminous plant, the method comprising the steps of:
  (a) providing a quarter-seed meristem explant comprising the whole embryo of a source leguminous seed, wherein one-quarter of the cotyledon is left attached to the whole embryo, wherein the shoot apical meristem tissue of the whole embryo is intact and is exposed by removal of all primary leaves, and wherein the radicle tip is trimmed;
  (b) contacting the quarter-seed meristem explant with a hypertonic medium;
  (c) contacting the explant with a suspension of a bacterial transformation vector comprising a transformation construct;
  (d) co-cultivating the explant;
  (e) partially embedding the trimmed radicle end of the explant in shoot induction medium with the meristem side facing up;
  (f) incubating 3-6 weeks with biweekly changes to fresh shoot induction medium; and
  (g) transferring to shoot elongation medium;
  whereby a rooted leguminous plantlet that comprises transformed germline cells having at least one genetic modification, in comparison to the unmodified genome of the embryo of the source leguminous seed, effected by the transformation construct is regenerated without transition through a callus phase and at a transformation efficiency of at least about 30%.

Embodiment 2: The method of embodiment 1, wherein the leguminous plant is selected from the group consisting of *Phaseolus* spp., *Vigna* spp., *Vicia* spp., *Pisum* spp., *Lens* spp., *Glycine* spp., *Cajanus* spp., *Cicer* spp., *Medicago* spp., and *Trifolium* spp.

Embodiment 3: The method of embodiment 1, wherein the leguminous plant is *Glycine max* (soybean).

Embodiment 4: The method of embodiment 1, wherein the leguminous plant is elite soybean germplasm.

Embodiment 5: The method of embodiment 1, wherein the leguminous plant is an inbred soybean line.

Embodiment 6: The method of embodiment 1, wherein the source leguminous seed is selected from the group consisting of: (a) an immature leguminous seed; (b) a mature, imbibed leguminous seed; and (c) a germinated leguminous seed.

Embodiment 7: The method of embodiment 1, wherein the source leguminous seed is selected from the group consisting of: (a) an immature soybean seed; (b) a mature, imbibed soybean seed; and (c) a germinated soybean seed.

Embodiment 8: The method of any of embodiments 1-7, further comprising a selection step.

Embodiment 9: The method of any of embodiments 1-8, wherein the hypertonic medium has a higher specific osmotic pressure relative to the intercellular osmotic pressure of the meristem tissue.

Embodiment 10: The method of any of embodiments 1-9, wherein the hypertonic medium comprises MES (2-(N-morpholino)ethanesulfonic acid).

Embodiment 11: The method of any of embodiments 1-10, wherein the hypertonic medium comprises L-proline.

Embodiment 12: The method of any of embodiments 1-11, wherein the hypertonic medium does not comprise a growth hormone.

Embodiment 13: The method of any of embodiments 1-7 and 9-12, wherein the hypertonic medium does not comprise a selection agent.

Embodiment 14: The method of any of embodiments 1-13, wherein the hypertonic medium is a liquid or gel or solid.

Embodiment 15: The method of any of embodiments 1-14, wherein the contacting of the explant with the hypertonic medium is carried out for at least about 30 minutes.

Embodiment 16: The method of any of embodiments 1-15, wherein the contacting of the explant with the hypertonic medium is carried out for 1 to 4 hours or between 1 to 4 hours.

Embodiment 17: The method of any of embodiments 1-16, wherein the bacterial transformation vector is an *Agrobacterium* sp.

Embodiment 18: The method of embodiment 17, wherein the bacterial transformation vector is *Agrobacterium tumefaciens*.

Embodiment 19: The method of any of embodiments 1-17, wherein the transformation construct comprises: (a) DNA comprising left border and right border T-DNA sequences; (b) DNA encoding an RNA-guided nuclease; (c) DNA encoding a guide RNA; (d) DNA encoding a donor polynucleotide; or (e) a combination of any two or more of (a)-(d).

Embodiment 20: The method of any of embodiments 1-7 and 9-19, wherein the transformation construct does not encode a selectable marker.

Embodiment 21: The method of any of embodiments 1-20, wherein transformation efficiency is at least 30%.

Embodiment 22: The method of any of embodiments 1-20, wherein transformation efficiency is at least 40%.

Embodiment 23: The method of any of embodiments 1-20, wherein transformation efficiency is at least 50%.

Embodiment 24: The method of any of embodiments 1-20, wherein transformation efficiency is at least 60%.

Embodiment 25: The method of any of embodiments 1-24, wherein the rooted leguminous plantlet is regenerated within about 8 weeks from the time of inoculation.

Embodiment 26: The method of any of embodiments 1-25, wherein the regenerated leguminous plantlet is fertile.

Embodiment 27: The method of any of embodiments 1-26, further comprising the step of growing the regenerated leguminous plantlet to maturity, thus providing a mature transformed leguminous plant.

Embodiment 28: The method of embodiment 27, wherein the mature transformed leguminous plant has a genome that is greater than 99.9% identical to that of the embryo of the source leguminous seed.

Embodiment 29: The method of any of embodiments 27-28, further comprising recovering T1 seeds from the mature transformed leguminous plant.

Embodiment 30: The method of embodiment 29, further comprising growing a progeny transformed leguminous plant from the T1 seed.

Embodiment 31: The mature transformed leguminous plant produced by the method of embodiment 27.

Embodiment 32: Progeny leguminous seed or progeny leguminous plants produced from the mature leguminous soybean plant of embodiment 27.

Embodiment 33: The method of any of embodiments 1-25, wherein the leguminous plant is soybean, and wherein the regenerated soybean plantlet is fertile.

Embodiment 34: The method of any of embodiments 1-26, further comprising the step of growing the regenerated soybean plantlet to maturity, thus providing a mature transformed soybean plant.

Embodiment 35: The method of embodiment 34, wherein the mature transformed soybean plant has a genome that is greater than 99.9% identical to that of the embryo of the source soybean seed.

Embodiment 36: The method of any of embodiments 34-35, further comprising recovering T1 seeds from the mature transformed soybean plant.

Embodiment 37: The method of embodiment 36, further comprising growing a progeny transformed soybean plant from the T1 seed.

Embodiment 38: The mature transformed soybean plant produced by the method of embodiment 34.

Embodiment 39: Progeny soybean seed or progeny soybean plants produced from the mature transformed soybean plant of embodiment 34.

Embodiment 40: A system for bacterially mediated plant transformation comprising (a) a dicot meristem explant that has been contacted with a hypertonic medium, and (b) a bacterial transformation vector comprising a transformation construct.

Embodiment 41: The system of embodiment 40, wherein the dicot meristem explant is of a leguminous plant.

Embodiment 42: The system of any of embodiments 40-41, wherein the dicot meristem explant is of a soybean plant.

Embodiment 43: The system of any of embodiments 40-42, wherein the hypertonic medium comprises MES (2-(N-morpholino)ethanesulfonic acid).

Embodiment 44: The system of any of embodiments 40-43, wherein the hypertonic medium comprises L-proline.

Embodiment 45: The system of any of embodiments 40-44, wherein the hypertonic medium does not comprise a growth hormone.

Embodiment 46: The system of any of embodiments 40-45, wherein the hypertonic medium does not comprise a selection agent.

Embodiment 47: The system of any of embodiments 40-46, wherein the bacterial transformation vector is selected from *Agrobacterium* spp., *Rhizobium* spp., *Mesorhizobium loti*, *Sinorhizobium meliloti*, and *Ensifer adhaerens*.

Embodiment 48: The system of any of embodiments 40-46, wherein the bacterial transformation vector is *Agrobacterium tumefaciens*.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this invention have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest. All such similar substitutes and modifications apparent to those skilled in the art are deemed to be within the spirit, scope, and concept of the invention as encompassed by the embodiments of the inventions recited herein and the specification and appended claims.

What is claimed is:

1. A method of providing a transformed soybean plant, the method comprising the steps of:
    (a) providing a soybean plant quarter-seed meristem explant comprising the whole embryo of a source soybean seed, wherein the upper half of one cotyledon is left attached to the whole embryo and one cotyledon is completely removed, wherein the shoot apical meristem tissue of the whole embryo is intact and is exposed by removal of all primary leaves, and wherein the radicle tip is trimmed;
    (b) contacting the quarter-seed meristem explant with a hypertonic medium;
    (c) contacting the explant with a suspension of *Agrobacterium* comprising a transformation construct;
    (d) co-cultivating the explant 4-5 days;
    (e) partially embedding the trimmed radicle end of the explant in shoot induction medium with the meristem side facing up and with the hypocotyl positioned upright;
    (f) incubating with biweekly changes to fresh shoot induction medium; and
    (g) transferring to shoot elongation medium;
    whereby a rooted soybean plantlet that comprises transformed germline cells having at least one genetic modification, in comparison to the unmodified genome of the embryo of the source soybean seed, effected by the transformation construct is regenerated within 8 weeks from the time of inoculation, without transition through a callus phase and at a transformation efficiency of at least 30%.

2. The method of claim 1, wherein the soybean plant is (a) of elite soybean germplasm, or (b) an inbred soybean line.

3. The method of claim 1, wherein the source soybean seed is selected from the group consisting of: (a) an immature soybean seed; (b) a mature, imbibed soybean seed; and (c) a germinated soybean seed.

4. The method of claim 1, wherein the hypertonic medium comprises at least one of: (a) 2-(N-morpholino)ethanesulfonic acid (MES) or (b) L-proline.

5. The method of claim 1, wherein the hypertonic medium does not comprise at least one of: (a) a growth hormone or (b) a selection agent.

6. The method of claim 1, wherein the transformation construct comprises: (a) DNA comprising left border and right border T-DNA sequences that optionally flank an expression cassette; (b) DNA encoding an RNA-guided nuclease; (c) DNA encoding a guide RNA; (d) DNA encoding a donor polynucleotide; or (e) a combination of any two or more of (a)-(d).

7. The method of claim 1, wherein the transformation construct does not encode a selectable marker.

8. The method of claim 1, wherein transformation efficiency is at least 30%.

9. The method of claim 1, wherein the regenerated soybean plantlet is fertile.

10. The method of claim 1, further comprising the step of growing the regenerated soybean plantlet to maturity, thus providing a mature transformed soybean T0 plant.

11. The method of claim 10, wherein the mature transformed soybean T0 plant has a genome that is greater than 99.9% identical to that of the embryo of the source soybean seed.

12. The method of claim 10, further comprising recovering T1 seeds from the mature transformed soybean T0 plant.

13. The method of claim 12, further comprising growing a progeny transformed soybean T1 plant from the T1 seed.

14. A system for *Agrobacterium* mediated plant transformation comprising (a) a soybean plant quarter-seed meristem explant that has been pre-treated with a hypertonic medium that does not comprise a growth hormone or a selection agent, wherein the quarter-seed meristem explant comprises the whole embryo of a source soybean seed, wherein the upper half of one cotyledon is left attached to the whole embryo and one cotyledon is completely removed, wherein the shoot apical meristem tissue of the whole embryo is intact and is exposed by removal of all primary leaves, and wherein the radicle tip is trimmed; and (b) an *Agrobacterium* comprising a transformation construct, whereby the system leads to improved transformation efficiency such that a rooted soybean plantlet that comprises transformed germline cells having at least one genetic modification, in comparison to the unmodified genome of the embryo of the source soybean seed, effected by the transformation construct, is regenerated within 8 weeks from the time of inoculation, without transition through a callus phase and at a transformation efficiency of at least 30%.

15. The system of claim 14, wherein the hypertonic medium comprises at least one of: (a) MES or (b) L-proline.

16. The system of claim 14, wherein the *Agrobacterium* comprising the transformation construct is *Agrobacterium tumefaciens*.

17. The system of claim 14, wherein the transformation construct comprises: (a) DNA comprising left border and right border T-DNA sequences that optionally flank an expression cassette; (b) DNA encoding an RNA-guided nuclease; (c) DNA encoding a guide RNA; (d) DNA encoding a donor polynucleotide; or (e) a combination of any two or more of (a)-(d).

18. The method of claim 1, wherein the hypertonic medium has a higher specific osmotic pressure relative to the intercellular osmotic pressure of the meristem tissue.

19. The method of claim 1, wherein the hypertonic medium comprises MES, mannitol, sorbitol, and L-proline.

* * * * *